(12) United States Patent
Kawamata et al.

(10) Patent No.: US 7,388,030 B2
(45) Date of Patent: Jun. 17, 2008

(54) SUPPRESSORS OF ANEMIA AND APPETITE SUPPRESSORS AND METHODS FOR SUPPRESSING ANEMIA AND SUPPRESSING APPETITE

(75) Inventors: Yasuko Kawamata, Kawasaki (JP); Takeshi Kimura, Kawasaki (JP); Makoto Miura, Kawasaki (JP); Sakino Toue, Kawasaki (JP); Ryousei Sakai, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 333 days.

(21) Appl. No.: 10/851,338

(22) Filed: May 24, 2004

(65) Prior Publication Data

US 2004/0214894 A1    Oct. 28, 2004

Related U.S. Application Data

(62) Division of application No. 10/158,059, filed on May 31, 2002, now abandoned.

(30) Foreign Application Priority Data

| May 31, 2001 | (JP) | ............................. 2001-165242 |
| May 24, 2002 | (JP) | ............................. 2002-150918 |

(51) Int. Cl.
*A61K 31/198* (2006.01)
(52) U.S. Cl. ...................................... 514/561; 514/562
(58) Field of Classification Search ................ 514/561
See application file for complete search history.

(56) References Cited

U.S. PATENT DOCUMENTS

| 4,042,687 | A | * | 8/1977 | Gans et al. .................... 514/21 |
| 4,042,688 | A | * | 8/1977 | Gans et al. .................... 514/21 |
| 4,368,204 | A | | 1/1983 | Sato et al. |
| 5,132,113 | A | | 7/1992 | Luca |
| 5,273,754 | A | * | 12/1993 | Mann ......................... 424/440 |
| 6,274,612 | B1 | | 8/2001 | Bryan |
| 6,313,170 | B1 | | 11/2001 | Yu et al. |
| 6,420,350 | B1 | * | 7/2002 | Fleischner .................... 514/62 |
| 6,468,988 | B1 | * | 10/2002 | Mann ........................... 514/58 |

FOREIGN PATENT DOCUMENTS

| FR | 2 628 298 | 9/1989 |
| JP | 6-24977 | 2/1994 |
| JP | 9-157163 | 6/1997 |
| JP | 2001-165242 | 5/2001 |
| JP | 2002-150918 | 5/2002 |

OTHER PUBLICATIONS

"Appetite Suppressant Activity of Supplemental Dietary Amino Acids and Subsequent Compensatory Growth of Broilers", Acar et al., 2001 Poultry Science, 80:1215-1222.*
I. Kaldor, *Austral. J. exp. Biol.*, vol. 32, pp. 795-799 (1954).
K. Muramatsu, *Journal of Japanese Society of Nutrition and Food Science*, vol. 37, No. 5, pp. 399-418 (1984).
K. Sugiyama, et al., *J. Nutr. Sci. Vitaminol.*, vol. 33, pp. 195-205 (1987).
A. Harper et al, "Effects of Ingestion of Disproportionate Amounts of Amino Acids", *Physiological Reviews*, vol. 50, No. 3, Jul. 1970, pp. 428-429 and 452-465.
F. Yokota et al, "Nutritional Anemia Induced By Excess Methionine in Rate and the Alleviative Effects of Glycine on it", *J. Nutr. Sci. Vitaminol.*, vol. 24, 1978, pp. 527-533.
R. Steele et al, "Effects of Dietary 3-Methylthiopropionate on Metabolism, Growth and Hematopoiesis in the Rat", *J. Nutr.*, vol. 109, 1979, pp. 1739-1251.
J.M. Harter, et al., *Journal of Nutrition*, vol. 108, No. 7, pp. 1061-1070 (1978).
D. Fau, et al., *Journal of Nutrition*, vol. 117, No. 11, pp. 1838-1843 (1987).
Derwent Publications, AN 1994-071836, XP-002221330 (1994) (corresponds to JP 6-24977).
Derwent Publications, AN 1997-369377, XP-002221329 (1997) (corresponds to JP 9-157163).

* cited by examiner

*Primary Examiner*—Brian Kwon
(74) *Attorney, Agent, or Firm*—Oblon, Spivak, McClelland, Maier & Neustadt, P.C.

(57) ABSTRACT

The present invention provides a method for suppressing hemolytic anemia by selectively ameliorating reticulocyte increase and iron deposition on spleen caused as the side effects of methionine. The present invention also provides an appetite suppressor with reduced such side effects, where threonine is used as the effective ingredient of the suppressor of hemolytic anemia due to methionine and a combination of methionine and threonine is used as the effective ingredient of the appetite suppressor.

5 Claims, 1 Drawing Sheet

SUPPRESSORS OF ANEMIA AND APPETITE SUPPRESSORS AND METHODS FOR SUPPRESSING ANEMIA AND SUPPRESSING APPETITE

CROSS REFERENCES TO RELATED APPLICATIONS

This application claims priority to Japanese Patent Application No. 2001-165242, which was filed on May 31, 2001, and Internal Japanese Patent Application No. 2002-150918, which was filed on May 24, 2002, both of which are incorporated herein by reference in their entirety.

BACKGROUND OF THE INVENTION

Field of the Invention

The present invention relates to novel suppressors of anemia and novel appetite suppressors. More specifically, the present invention relates to agents for the prophylaxis (prevention), amelioration (improvement) and/or therapeutic treatment of anemia due to or caused by methionine (methionine-induced anemia). The present invention also relates to methionine-containing appetite suppressors, which exhibit a reduced tendency to elicit anemia. The present invention further relates to feeds, nutritional supplements, foods or drinks, and/or pharmaceutical agents, which contain methionine and in which the tendency or action of methionine to elicit hemolytic anemia is ameliorated or reduced (improved). The present invention additionally relates to methods for suppressing methionine-induced anemia. The present invention also relates to methods for suppressing the appetite.

DISCUSSION OF THE BACKGROUND

Methionine belongs to a group of sulfur-containing amino acids and is one of the essential amino acids for humans. Methionine is nutritionally important. It is known that methionine is abundantly present in animal-derived proteins but is present in lesser amounts in plant-derived proteins. Methionine is medicinally used in amino acid infusions and general amino acid formulations in blends with other essential amino acids. Methionine is also used in therapeutic agents for liver diseases such as chronic or acute hepatitis and liver cirrhosis and in agents for the detoxification of chemicals, owing to its anti-fatty liver action and detoxification action (see "*General Review of Amino Acid Industry (Aminosan Kogyo no Zenyou)*," CMC, pp. 29-39, 1988).

However, it is known that large doses of methionine act to suppress body weight increase or even to decrease body weight owing to appetite loss (appetite lowering), as well as induce (cause) the occurrence of hemolytic anemia with main symptoms such as an increase in reticulocytes and iron deposition on the spleen, and the like. Such actions are problematic for use the use of methionine in the pharmaceutical field and in the field of food products.

To overcome these problems (for the attenuation of these methionine actions), Muramatsu (see "*Journal of Japanese Society of Nutrition and Food Science (Nihon Eiyo Shokuryo Gakkai Shi)*," vol. 37, pp. 399-418 (1984)) and Sugiyama et al. (see "*J. Nutr. Sci. Vitaminol.*," vol. 33, pp. 195-205 (1987)) have proposed methods for ameliorating the symptoms involved in hemolytic anemia and appetite loss (appetite lowering), by using serine and glycine in combination with methionine. However, no report has been issued yet about any method for selectively attenuating the actions or effects of methionine.

Thus, there remains a need for methods for suppressing methionine-induced anemia. There also remains a need for methods for selectively suppressing the adverse effects (i.e., anemia) caused by methionine when using methionine as an appetite suppressor. There further remains a need for compositions which are effective for carrying out these methods.

SUMMARY OF THE INVENTION

Accordingly, it is one object of the present invention to provide novel suppressors of anemia.

It is another object of the present invention to provide novel agents effective for suppressing methionine-induced anemia.

It is another object of the present invention to provide novel appetite suppressors.

It is another object of the present invention to provide novel appetite suppressors which contain methionine and which exhibit a reduced tendency to cause anemia.

It is another object of the present invention to provide novel pharmaceutical agents capable of preventing, ameliorating and/or therapeutically treating anemia due to or caused by methionine, namely a suppressor of anemia.

It is another object of the present invention to provide novel pharmaceutical agents which are effective for suppressing the appetite, while also selectively suppressing an the action of eliciting anemia.

It is another object of the present invention to provide novel methods for suppressing, ameliorating, or treating anemia.

It is another object of the present invention to provide novel methods for suppressing, ameliorating, or treating methionine-induced anemia.

It is another object of the present invention to provide novel methods for suppressing the appetite.

It is another object of the present invention to provide novel methods for suppressing the appetite, while at the same time suppressing, ameliorating, or treating anemia.

It is another object of the present invention to provide novel methods for suppressing the appetite, while at the same time suppressing, ameliorating, or treating methionine-induced anemia.

These and other objects, which will become apparent during the following detailed description, have been achieved by the inventors' discovery that although the two effects of methionine, i.e., eliciting hemolytic anemia and suppressing the appetite, had previously been considered to work in combination, the methionine action of causing anemia, particularly hemolytic anemia with symptoms including reticulocyte increase and iron deposition on the spleen can be suppressed selectively and effectively by appropriate intake or dosing (administration) of threonine.

The inventors have also found that the intake or dosing of threonine in combination with methionine can selectively suppress the methionine action of inducing anemia without any influence on the appetite-suppressing action of methionine.

The inventors have also found that the L-form of threonine has a great safety profile on use and can be used in foods and drinks. Based on these various findings, the present invention has been achieved.

More specifically, in a first aspect the present invention provides a suppressor of methionine-induced anemia, where the suppressor characteristically contains (comprises) threonine, which may or may not be in a salt form. From the standpoint of optical isomer, threonine of L-form which is metabolizable in biological organisms may be used.

Further, the suppressor of anemia in accordance with the present invention can prevent, ameliorate and/or therapeutically treat anemia due to methionine, specifically hemolytic anemia, particularly reticulocyte increase and iron deposition on the spleen.

Thus, the anemia suppressor of the present invention may satisfactorily contain a substance with an action inducing hemolytic anemia, for example methionine in the pharmaceutical dosage form thereof. Otherwise, the suppressor of anemia may satisfactorily be in a dosage form of threonine alone. In this case, methionine may or may not be in a salt form. From the standpoint of optical isomer, additionally, the naturally occurring L-form is preferable but other isomers such as D-form may also be used. Alternatively, other amino acids may be used in combination.

Meanwhile, the suppressor of anemia may contain serine and glycine with an action to suppress anemia, but these are generated via the metabolism of threonine in biological organisms. Hence, these are almost unnecessary, and the present anemia suppressor may be substantially free of serine and/or glycine. In the context of the present invention, the term substantially free of serine and glycine means that the anemia suppressor contains less than 5% by weight, preferably less than 1% by weight, more preferably less than 0.1% by weight of serine and/or glycine based on the total weight of the anemia suppressor.

For the intake or dosing of the anemia suppressor of the present invention, the anemia suppressor can be incorporated or dosed in any form with no specific limitation. The anemia suppressor may be orally given or dosed in a simple manner.

The subject to be given or dosed is an animal utilizing methionine in particular, including for example humans. The subject preferably includes humans. The intake or dose of methionine in this case is preferably about (approximately) 25 to 100 mg/kg/day, more preferably about 25 to 85 mg/kg/day and further more preferably about 30 to 50 mg/kg/day on the basis of the free form thereof. The intake or dose of threonine is preferably about (approximately) 20 to 300 mg/kg/day, more preferably about 20 to 255 mg/kg/day and further more preferably about 30 to 80 mg/kg/day on the basis of the free form thereof.

Alternatively, the ratio of threonine to methionine is preferably at about (approximately) 80 to 300% (by weight) and more preferably about 100 to 160% (by weight) on the basis of the free form thereof.

The form of the anemia suppressor is not specifically limited to any form. Preferably, the anemia suppressor is in the form of a feed, nutritional supplement, drink or food (the generic name of drink products and food products) or pharmaceutical agent.

In another aspect, the present invention provides an appetite suppressor characteristically containing (comprising) methionine and threonine. That is, because threonine does not exert any effect on appetite loss caused as one of the methionine actions, an appetite suppressor containing methionine as the effective ingredient and threonine blended therein can be produced. In this case, methionine may or may not be in a salt form. Similarly, threonine may or may not be in a salt form. Concerning their optical isomers, further, the same as in the anemia suppressor is true with the appetite suppressor.

Methionine incorporated or dosed at 25 mg/kg/day or more may possibly induce an action to suppress appetite. If at least one of serine and glycine is contained therein, the action to suppress appetite is attenuated (improved) or treated. Hence, these two types of amino acids should not be contained therein, and the present appetite suppressor is preferably substantially free of serine and/or glycine. In the context of the present invention, the term substantially free of serine and glycine means that the anemia suppressor contains less than 5% by weight, preferably less than 1% by weight, more preferably less than 0.1% by weight of serine and/or glycine based on the total weight of the anemia suppressor.

When the appetite suppressor of the present invention is to be incorporated (given) or dosed, the form of the appetite suppressor is not specifically limited. However, the appetite suppressor is orally incorporated (given) or dosed in a conventional manner.

The subject to be given or dosed preferably includes humans or pet animals. In this case, the intake or dose of methionine is preferably about (approximately) 25 to 100 mg/kg/day, more preferably about 25 to 85 mg/kg/day, and further more preferably about 30 to 50 mg/kg/day, on the basis of the free form thereof. The intake or dose of threonine is preferably about (approximately) 20 to 300 mg/kg/day, more preferably about 20 to 255 mg/kg/day, and further more preferably about 30 to 80 mg/kg/day, on the basis of the free form thereof.

Alternatively, the ratio of threonine to methionine is preferably at about (approximately) 80 to 300% (by weight) and more preferably about 100 to 160% (by weight) on the basis of the free form thereof.

The form of the appetite suppressor is not specifically limited to any form. Preferably, the appetite suppressor is in the forms of a feed, nutritional supplement, drink or food, or pharmaceutical agent. Additionally, the appetite suppressor may be in the forms of a diet food or specific health food.

Another embodiment of the present invention is a methionine-containing feed, nutrient supplement, food or drink or pharmaceutical agent, which characteristically contains (comprises) threonine to ameliorate (improve) hemolytic anemia due to methionine.

In accordance with the present invention, threonine is used in combination, so as to suppress the above described action of methionine. As for the method of the use and the like, the descriptions of the above described two embodiments of the present invention can be referenced.

In addition, the following embodiments are also provided by in the present invention, as other aspects thereof.

A method for suppressing methionine-induced anemia, which comprises administrating threonine, which may or may not be in a salt form, to a living subject.

A method for suppressing appetite, which comprises administrating methionine and threonine to a living subject, where methionine may or may not be in a salt form and threonine also may or may not be in a salt form.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

Figure 1:
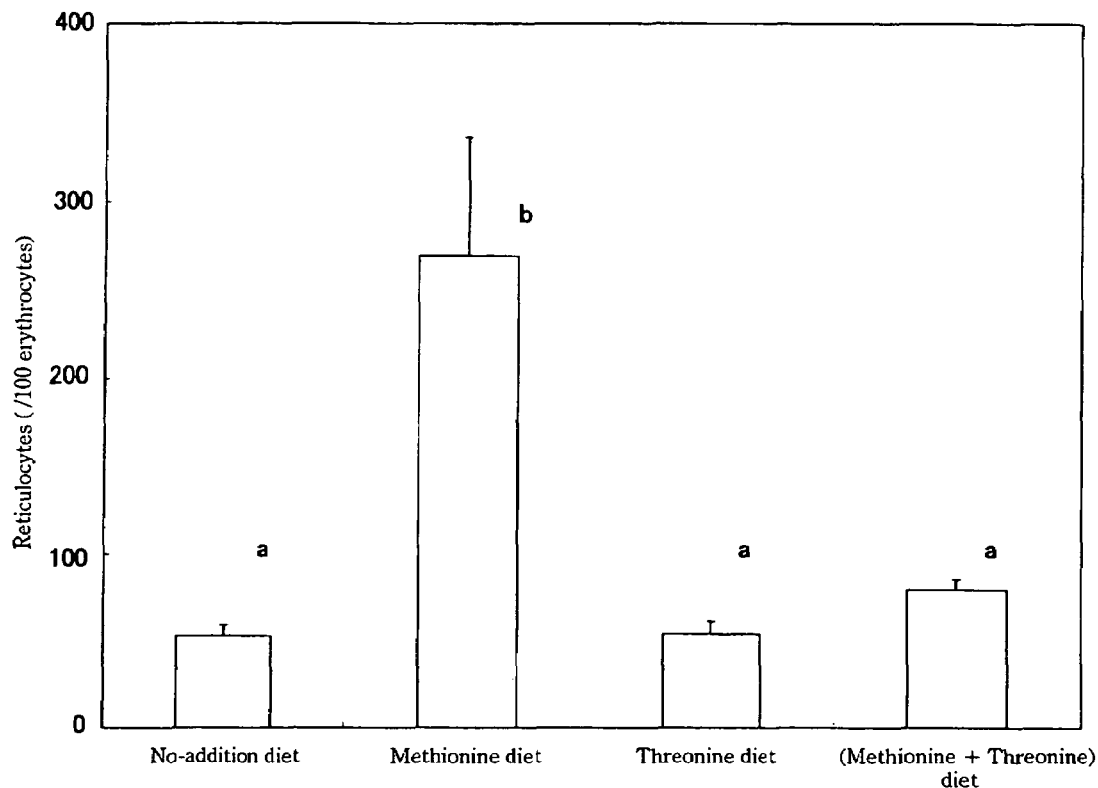
FIG. 1 shows a comparison of the reticulocyte counts in rat blood among the individual experimental diet groups in Example 1 (mean±SD; n=6).

Regarding the symbols: a, b and c in the above figures, it shows that among or between groups with different symbols of "a," "b," and "c," there is a statistical significant difference (level of significance: 5%).

DETAILED DESCRIPTION OF THE PREFERRED EMBODIMENTS

The present invention encompasses a number of embodiments, namely a suppressor of anemia due to methionine; an appetite suppressor; a feed, a nutritional supplement, a food or drink, or a pharmaceutical agent, where the hemolytic anemia due to methionine is ameliorated; a method of suppressing anemia; a method of suppressing the appetite; and also some other embodiments thereof described above.

I. Anemia Suppressor:

The anemia suppressor in accordance with the present invention is a pharmaceutical agent for suppressing anemia due to methionine, particularly hemolytic anemia, namely hemolytic anemia with symptoms such as an increase of reticulocytes and iron deposition on the spleen.

The term "reticulocyte" means juvenile erythrocyte. The increase of reticulocytes indicates the presence of a phenomenon of vigorous erythrocyte regeneration, namely the presence of anemia or anemia tendency. Further, the activation of abnormal erythrocyte damage in the spleen following the increase of abnormal erythrocytes, which is the etiology of erythrocyte decrease, may sometimes deposit iron derived from abnormal erythrocytes on spleen.

Methionine has traditionally been used in pharmaceutical uses, for example as an ingredient of amino acid infusions and general amino acid dosage forms. Methionine is also used in dosage forms to maintain or control liver functions, via the anti-fatty liver action and is additionally used for the detoxification of poisonous chemicals, via the detoxification action.

However, when administered by itself without any other amino acid components (amino acid(s)) which effect the reduction of the side effects, methionine may potentially cause the occurrence of actions (side effects) such as an increase of reticulocytes and iron deposition on the spleen. To suppress such side effects in accordance with the present invention, threonine preliminarily blended homogenously with methionine in a methionine dosage form (preparation) can selectively and effectively prevent these side effects. Various foods and drinks prepared by active use of the methionine ingredient (methionine or the like) have been known. The combined use of threonine as described above can bring about the same effect.

Alternatively, threonine suppresses methionine-induced anemia, with no or almost no emergence of any new side effects. Thus, threonine can suppress the side effect described above selectively and effectively. Hence, threonine is promising for use as a suppressor of anemia due to methionine in the fields of feeds, nutritional supplements, foods and drinks and pharmaceutical products, and particularly where methionine is used.

The suppressor of methionine-induced anemia of the present invention is not specifically limited to any form for human intake or human dosing. Accordingly, various dosage forms such as oral intake, oral dosing or parenteral dosing (parenteral administration)(intravenous dosing and the like) are possibly employed. In regard to simplicity, oral intake or oral dosing is preferable. Because the anemia suppressor can be used in mixture in a product using methionine in a simple manner, the product using methionine is discussed below.

The anemia suppressor of the present invention can be used in a dosage form containing methionine and threonine and may satisfactorily contain various formulation substances pharmacologically acceptable (as auxiliary substances) (which may be referred to as "pharmaceutically acceptable carriers" hereinbelow). The formulation (preparation) substances can be selected appropriately, depending on the dosage form of the suppressor of anemia. The formulation substances may be for example excipients, diluents, additives, disintegrators (disintegrants), binders, coating agents, lubricants, smoothing agents, lubricant pharmaceuticals (lubricants), flavoring agents, sweeteners, solubilization agents and the like. Further, the formulation substances specifically include for example magnesium carbonate, titanium dioxide, lactose, mannitol and other sugars, talc, milk protein, gelatin, starch, cellulose and derivatives thereof, animal and vegetable oils, polyethylene glycol, and solvents, for example sterile water and monovalent or polyvalent alcohols, for example glycerol.

The anemia suppressor of the present invention can be prepared in various pharmaceutical dosage (preparation) forms known as described above or to be possibly developed in future, for example various dosage forms for oral dosing, intraperitoneal dosing, transdermal dosing, and inhalation dosing. To prepare the pharmaceutical agent of the present invention into these various pharmaceutical dosage forms, known methods or those to be possibly developed in future can appropriately be employed.

These various pharmaceutical dosage forms (including nutritional supplements) include for example dosage forms in appropriate solids or liquids, which are for example granules, powders, coated tablets, tablets, (micro)capsules, suppositories, syrups, juices, suspensions, emulsions, infusions (dropping agents), solutions for injections, and dosage forms of sustained release types of active substance.

As for quantities of the methionine and threonine used, it is needless to say that the suppressor of anemia in one of the dosage forms described above in accordance with the present invention should contain the above described ingredients (methionine and threonine) at quantities effective for the exertion of their pharmaceutical efficacies.

The subject to be given or dosed includes animals utilizing methionine in particular, for example humans. The subject preferably includes humans. The intake or administration dose of methionine in this case is preferably about (approximately) 25 to 100 mg/kg/day, more preferably about 25 to 85 mg/kg/day and further more preferably about 30 to 50 mg/kg/day on the basis of the free form thereof. The intake or administration dose of threonine is preferably about (approximately) 20 to 300 mg/kg/day, more preferably about 20 to 255 mg/kg/day and further more preferably about 30 to 80 mg/kg/day on the basis of the free form thereof.

Alternatively, the content of threonine to methionine is preferably at about (approximately) 80 to 300% (by weight) and more preferably about 100 to 160% (by weight) on the basis of the free forms thereof.

Embodiments of its application to pharmaceutical products have been described above. Based on the embodiments, the present anemia suppressor is easily applicable to feeds, nutritional supplements, and foods and drinks. Generally, threonine is added for the purpose of suppressing the above described side effects in methionine products. The object product can be obtained or recovered at a state such that a given quantity of threonine is homogenously mixed with methionine.

II. Appetite Suppressor:

An appetite suppressor is now described as a second embodiment of the present invention.

In accordance with the present invention, methionine-induced hemolytic anemia involving symptoms such as reticulocyte increase and iron deposition on the spleen as described above can be suppressed by using methionine and threonine in combination, without any influence on the methionine action to suppress appetite. The action is effectively utilized in accordance with the present invention.

The appetite suppressor of the present invention will now be described in more detail hereinbelow.

As described above, methionine when used singly in various products exerts its actions such as reticulocyte increase and iron deposition on the spleen, as well as an action to suppress appetite. Threonine preliminarily contained together with methionine in such products can selectively and effectively suppress the action of causing anemia. In other words, the threonine action of suppressing anemia together with the methionine action of suppressing appetite can singly be utilized in an effective manner.

Alternatively, threonine exerts its action of suppressing anemia selectively and effectively when threonine is contained together with methionine as described above. Additionally, the resulting formulation can also suppress appetite with no or almost no emergence of other side effects. Thus, the combined use of methionine and threonine is quite promising for an appetite suppressor.

Like the anemia suppressor, the appetite suppressor of the present invention may be used in the form of a pharmaceutical product (including nutritional supplements) and may contain various formulation substances pharmacologically acceptable (as auxiliary substances) (which may be also referred to as "pharmaceutically acceptable carriers"). The formulation substances may be appropriately selected, depending on the dosage form of the formulation (preparation) thereof. The formulation substances may be for example excipients, diluents, additives, disintegrators, binders, coating agents, lubricants, smoothing agents, lubricant pharmaceuticals (lubricants), flavoring agents, sweeteners, and solubilization agents. Further, the formulation substances are specifically for example magnesium carbonate, titanium dioxide, lactose, mannitol and other sugars, talc, milk protein, gelatin, starch, cellulose and derivatives thereof, animal and vegetable oils, polyethylene glycol, and solvents, for example sterile water and monovalent or polyvalent alcohols, for example glycerol.

These various pharmaceutical dosage (preparation) forms include for example dosage forms in appropriate solids or liquids, which are for example granules, powders, coated tablets, tablets, (micro)capsules, suppositories, syrups, juices, suspensions, emulsions, infusions (dropping agents), solutions for injections, and dosage forms sustaining the release of an active substance.

As for quantities of methionine and threonine, it is needless to say that the appetite suppressor in one of the dosage forms described above in accordance with the present invention should contain the ingredients (methionine and threonine) at quantities effective for the exertion of their pharmaceutical efficacies.

The application of the present invention to pharmaceutical products has been described above. Methionine combined with threonine when used in foods and drinks can exert the effects described above. Accordingly, the present invention is expected to be applicable to these foods and drinks, particularly those using methionine.

For the appetite suppressor of the present invention, embodiments of various nutritious supplements, foods and drinks or pharmaceutical products having been known or being possibly developed in future can be selected appropriately. Embodiments of diet foods or specific health food products can be also selected.

The embodiments for various foods and drinks and the like as the appetite suppressors in various forms (products) include for example sweets (cool sherbet, jelly, cake, candy), bread, chewing gum and products for animals (pets) except for humans. In such manner, embodiments of products with the additional appetite-suppressing action are also encompassed within the scope of the present invention.

The subject to which the appetite suppressor of the present invention is given or dosed is not specifically limited but preferably includes humans and pet animals. The form of the intake or dosing in this case is not specifically limited. Thus, various dosing forms may be selected, including for example oral intake, oral dosing, and parenteral dosing (intravenous dosing and the like). From the standpoint of simplicity, oral intake or oral dosing is preferable. It has been known that methionine acts to suppress the appetite and the use of methionine for the purpose has also been known. For the known use of methionine, threonine is homogenously mixed with methionine for use in combination.

The intake or dose of methionine in this case is preferably about (approximately) 25 to 100 mg/kg/day, more preferably about 25 to 85 mg/kg/day, and further more preferably about 30 to 50 mg/kg/day, on the basis of the free form thereof. The intake or dose of threonine is preferably about (approximately) 20 to 300 mg/kg/day, more preferably about 20 to 255 mg/kg/day, and further more preferably about 30 to 80 mg/kg/day, on the basis of the free form thereof.

Alternatively, the ratio of threonine to methionine is preferably at about (approximately) 80 to 300% (by weight) and more preferably about 100 to 160% (by weight) on the basis of the free form thereof.

Based on the descriptions above, the inventive appetite suppressor containing a combination of threonine and methionine can selectively and effectively suppress the action of methionine to cause anemia, so that only the appetite-suppressing action can be effectively utilized. Hence, the pharmaceutical agent can readily be used practically.

III. Nutritional Supplements, Foods and Drinks, or Pharmaceutical Products:

An additional embodiment of the present invention is a methionine-containing feed, nutritional supplement, food or drink or pharmaceutical product, which characteristically contains (comprises) threonine and can ameliorate (improve) hemolytic anemia due to methionine.

The methods for using methionine and threonine are as described above in the two embodiments. Therefore, it is not at all difficult to practice this embodiment of the present invention.

For example, threonine (at a given amount) can be homogeneously mixed with methionine for use in known methionine-containing feeds, nutritional supplements, foods and drinks or pharmaceutical products, particularly in which it is intended to ameliorate the side effects of methionine.

As described above, the inventive products of feeds, nutritional supplements, foods and drinks or pharmaceutical products in which hemolytic anemia due to methionine is ameliorated can readily be produced or obtained, utilizing the descriptions of the above-described two embodiments of the present invention and known techniques.

The appetite loss or the suppression of body weight increase owing to a large dose of methionine has been known but the expression mechanism therefor has scarcely been known yet. A possibility cannot yet totally be eliminated that the rejection of the intake of methionine diet per se may directly lead to the emergence of these phenomena. The reason is that experimental animals in almost all the research tests were fed with experimental feeds in blend with methionine so the animals could not select experimental diets except for the methionine feeds. When animals happen to reject intake of such methionine diets, the animals may possibly reject the odor or taste of methionine per se or the odor or taste thereof occurring synergistically with other ingredients in the feeds. Further, it has been suggested that threonine does not have a suppressive action of appetite or body weight increase as strong as that of methionine (see Muramatsu, *Journal of Japanese Society of Nutrition and Food Science* (*Nihon Eiyo Shokuryo Gakkai Shi*), vol. 37, pp. 399-418 (1984)).

To verify the findings so far, therefore, simultaneous feeding experiments with two types of methionine diet and threonine diet were done as described below (see Example 5). The effect of methionine intake was verified.

IV. Method of Suppressing Anemia:

In this embodiment, the present invention provides a method for suppressing anemia, particularly anemia induced by the administration of methionine. The method comprises:

administering to subject in need thereof an effective amount of threonine.

In the context, of the present method of suppressing anemia, the form of the threonine may be as described above, in the context of the anemia suppressor. Moreover, the threonine may be administered in the same way as described above in the context of the anemia suppressor.

More specifically, the threonine is administered in an amount of about (approximately) 20 to 300 mg/kg/day, more preferably about 20 to 255 mg/kg/day, and even more preferably about 30 to 80 mg/kg/day, on the basis of the free form threonine. Such a dosage regimen may be maintained for a period of time ranging from the onset of anemia to the time of reduction of the symptoms of anemia. Alternatively, the dosage regimen may be commenced at the same time as the commencement of an appetite suppression program involving the administration of methionine and continued over the same period of time as the administration of methionine The threonine may be administered via any conventional route. Preferably, the threonine is administered orally. Even more preferably, the threonine is administered orally in the form of a nutritional supplement, food or drink, or pharmaceutical product.

As explained above, the present method is particularly effective for suppressing methionine-induced anemia. In such cases, the anemia is typically the result of methionine administration in the form of an appetite suppressant or for the other purposes described above. In such cases, the intake or dose of methionine is typically about (approximately) 25 to 100 mg/kg/day, preferably about 25 to 85 mg/kg/day, and more preferably about 30 to 50 mg/kg/day, on the basis of the free form of methionine.

Thus, in the present method for suppressing anemia, the subject being treated will typically be either suffering from methionine-induced anemia or at risk of developing methionine-induced anemia. Subjects suffering from methionine-induced anemia may be identified, e.g., by monitoring the level of reticulocytes in the blood. Patients or subjects who are at risk of developing methionine-induced anemia include those which are currently on a dietary program involving methionine administration or about to embark on a dietary program involving methionine administration.

V. Method of Suppressing the Appetite:

In another embodiment, the present invention provides a method of suppressing the appetite, comprising:

administering to subject in need thereof an appetite-suppressing effective amount of methionine and an anemia-suppressing effective amount of threonine.

In the context of the present method of suppressing the appetite, the form of the threonine may be the same as described above, in the context of the appetite suppressor. Moreover, the threonine may be administered in the same way as described above in the context of the anemia suppressor.

In this case, the intake or dose of methionine is preferably about (approximately) 25 to 100 mg/kg/day, more preferably about 25 to 85 mg/kg/day, and further more preferably about 30 to 50 mg/kg/day, on the basis of the free form of methionine. The intake or dose of threonine is preferably about (approximately) 20 to 300 mg/kg/day, more preferably about 20 to 255 mg/kg/day, and further more preferably about 30 to 80 mg/kg/day, on the basis of the free form of threonine.

Alternatively, the methionine and threonine may be administered in relative amounts such that the weight ratio of threonine to methionine is preferably about (approximately) 80 to 300% (by weight), and more preferably about 100 to 160% (by weight), on the basis of the free forms of threonine and methionine.

Such a dosage regimen may be maintained for as long as necessary or until a sufficient weight reduction has been obtained.

The methionine and threonine may be administered via any conventional route. Preferably, they are both administered orally. Even more preferably, the methionine and threonine are administered orally in the form of a nutritional supplement, food or drink, or pharmaceutical product. Although the threonine and methionine can be administered in separate forms or compositions, in a preferred embodiment, the methionine and threonine are administered together in the form of a single composition.

In the present method for suppressing the appetite, the subject being treated will typically be one requiring or desiring weight loss (i.e., one who is obese) or one at risk of gaining undesired weight or becoming obese.

Other features of the invention will become apparent in the course of the following descriptions of exemplary embodiments which are given for illustration of the invention and are not intended to be limiting thereof.

EXAMPLES

Example 1

Suppressive Effect on Reticulocyte Increase

Experimental Animals:

Male F344/DuCrj rats of age 4 weeks were purchased from Charles River Japan, Inc. The rats were placed and fed in bracket cages in environment at room temperature of about 25° C. and a relative humidity of about 60% in a bright/dark cycle where the bright stage was set from 7:00 to 19:00. After the animals were preliminarily fed with a commercially available powder feed CRF-1 (manufactured by Oriental Yeast Co., Ltd.) for one week and with the following no-addition diet for one week, 6 rats were randomly assigned per group. Then, the following experimental diets were fed ad libitum for 2 weeks. As drinking water, tap water was fed ad libitum.

Experimental Feeds:

No-addition diet was composed of β-cornstarch at 62.9%, casein at 20.0%, soybean oil at 7.0%, cellulose at 5.0%, AIN-93G mineral mix (Oriental Yeast Co., Ltd.) at 3.5%, AIN-93 vitamin mix (Oriental Yeast Co., Ltd.) at 1.0%, L-cystine at 0.3%, choline tartrate at 0.25% and t-butylhydroquinone at 0.0014%. The diet was essentially based on the US NRC AIN-93G purified feed composition (1995), but the α-cornstarch and sucrose in the original composition were totally substituted with (replaced by) β-cornstarch. When amino acid was to be contained in an experimental diet, the amino acid was substituted for a part of the β-cornstarch. When methionine or threonine was to be contained in an experimental diet, methionine and threonine were at 2.4% and 3.8%, respectively. When methionine and threonine were to be simultaneously contained in an experimental diet, methionine and threonine were at the same ratios as described above.

Amino Acids:

All amino acids used were amino acids (L-forms; free forms) manufactured by Ajinomoto Co., Inc. The same is true with the following Examples.

Various Measurements:

On day 14 after feeding with the individual experimental diets, the animals were anesthetized with ether; after laparotomy, blood was taken from abdominal inferior vena cava. Using blood treated with EDTA-2K for anti-coagulation, blood smear samples were prepared by the Brecher's method (see "Handbook of All Laboratory Test Techniques (Rinshou Kensa Gijvutsu Zensho)," vol. 3, Laboratory Blood Test, 1972). Reticulocytes were counted with an automatic blood image typing apparatus (Hitachi Type 8200).

Groups with the individual experimental diets were compared together by the Tukey's multiple comparison test. At the level of significance P<0.05, statistical significance was determined.

Results:

The no-addition diet and the threonine diet were fed to the rats. No increase of reticulocyte was observed. As described in the findings of the related art, the reticulocyte count was distinctly increased in the rats fed with the methionine diet. However, in a group simultaneously dosed with methionine and threonine, the increase of reticulocyte count as one of the indicators of hemolytic anemia was suppressed at almost the same level as in the no-addition group, which was a statistically significant effect (see FIG. 1). This indicates that simultaneous addition of threonine selectively suppresses the side effect of methionine.

Example 2

Suppressive Effect on Iron Deposition on the Spleen

The same experimental animals and experimental diets (feeds) as in Example 1 were used.

On day 14 after the feeding with the individual experimental diets, the animals under anesthesia with ether were exposed to exsanguination from abdominal aorta and bled to death, to resect spleen and weigh the weight. Immediately thereafter, the spleen was frozen in liquid nitrogen and stored in an ultra-low freezer.

After pulverizing the resected spleen under cooling in ice with Polytron, the non-heme iron content in the spleen was determined by absorptiometry with o-phenanthroline according to the Kaldor's method (see Austral. J. Exp. Biol., vol. 32, pp. 795-800 (1954)).

The items assayed for the individual groups fed with these experimental diets were compared together by the Tukey's multiple comparison test. At the level of significance P<0.05, statistical significance was determined.

Figure 2:
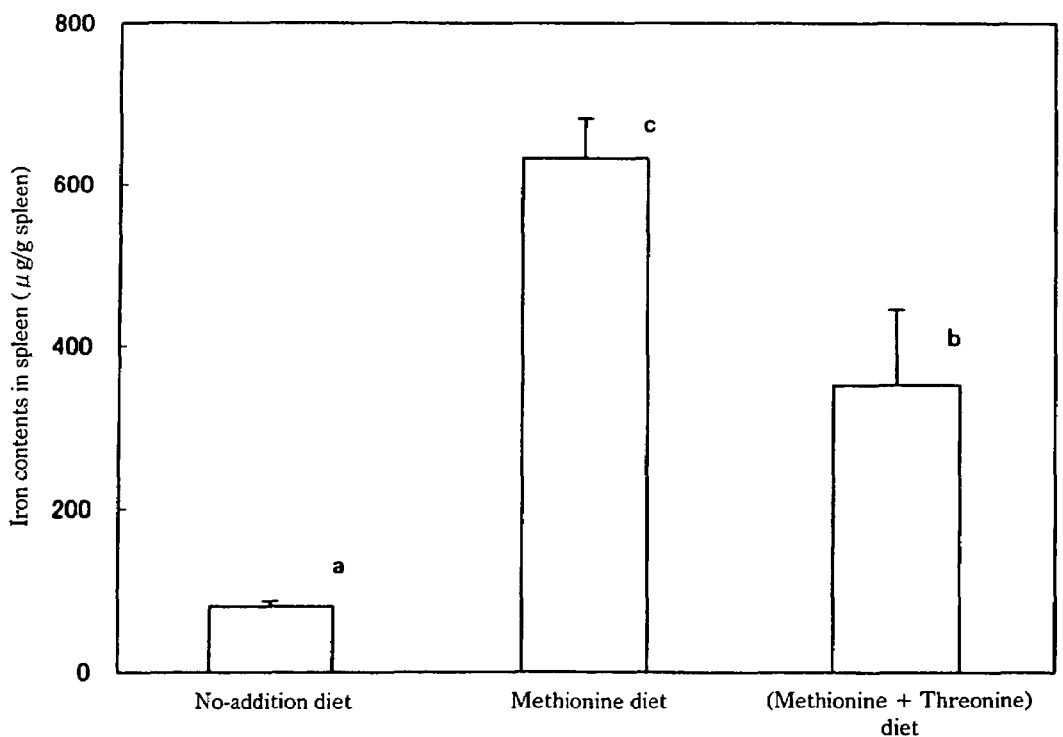
FIG. 2 shows a comparison of the heme iron contents in rat spleen among the individual experimental diet groups in Example 2 (mean±SD; n=6).

Results:

Iron deposition on spleen as another indicator of hemolytic anemia was examined. Compared with the group fed with the no-addition diet, the accumulated iron on spleen was distinctly increased in the rats fed with the methionine diet. However, the accumulated iron in the rats fed with the (methionine+threonine) diet was at a higher level than the normal level in the rats fed with the no-addition diet. Compared with the rats fed with the methionine diet, the iron accumulation in spleen in the rats fed with the (methionine+threonine) diet was significantly suppressed (see FIG. 2). This indicates that threonine added to the methionine diet possibly suppressed the onset of hemolytic anemia and consequently suppressed iron deposition on spleen.

Example 3

Effect on Appetite Loss

The same experimental animals were used as in Example 1. The same compositions of the experimental diets as in Example 1 were used. As amino acids to be contained, however, methionine, glycine and threonine were blended singly or in combination with methionine to 2.4%, 2.4% and 3.8%, respectively in experimental diets, by substituting the amino acids for a part of β-cornstarch.

Various Measurements:

Body weight and feed intake were measured daily. The total body weight increment and total intake over the 2 weeks during feeding with such experimental diets are shown below in the following Table 1.

TABLE 1

| Experimental diet fed | Body weight increment[1,2] (g/2 weeks) | Experimental diet intake[1,2] (g/2 weeks) |
|---|---|---|
| No-addition diet | 60.0 ± 5.2 ab | 175.9 ± 8.4 a |
| 2.4% methionine diet | 0.2 ± 2.3 e | 94.2 ± 4.5 b |
| 2.4% glycine diet | 66.2 ± 8.4 a | 184.0 ± 7.9 a |
| 3.8% threonine diet | 56.2 ± 6.3 bc | 173.5 ± 5.8 ac |
| 2.4% methionine + 2.4% glycine diet | 48.4 ± 6.0 c | 159.2 ± 10.0 c |
| 2.4% methionine + 3.8% threonine diet | 12.6 ± 3.9 d | 108.5 ± 4.7 b |

[1]mean ± standard deviation (SD); n = 6
[2]statistical significance among or between groups with different symbols "a" to "e" (at a 5% level of significance); no statistical significance among groups with identical symbols and with symbols including identical symbols.

Results:

Suppression of body weight and intake was distinctly demonstrated in the rats fed with the methionine diet. Based on the similar changes of the suppression of body weight increase and the suppression of intake among the experimental diets groups, it is indicated that the suppression of body weight increase may be caused by the suppression of intake and that the suppression of intake may potentially be caused by appetite loss.

Alternatively, such influences were never observed in the groups fed with the experimental diets singly blended with glycine or threonine. Further, the (methionine+glycine) diet was fed to the rats. Then, the influence observed in the rats fed with the methionine diet was greatly ameliorated (improved) in the groups fed with the (methionine+glycine) diet. In the (methionine+threonine) diet-fed group [(methionine+threonine) group], the body weight increase was improved at some extent, compared with the methionine diet-fed group. However, almost no change was observed in the intake between the (methionine+threonine) group and the methionine diet-fed group (methionine group). It is thought that based on these results, the effect of simultaneously ingested threonine on the suppression of appetite loss occurring due to a large excess intake of methionine is weaker than that of glycine or serine.

As described above, apparently, simultaneous intake of threonine with methionine is effective for selectively reducing the onset of the side effect induced by methionine intake, namely hemolytic anemia. Accordingly, such simultaneous threonine intake therewith allows the selective application of the methionine function, namely the action to decrease appetite.

Example 4

Effect on Appetite Loss in Different Animal Species and at Senile Stage

Experimental Animals:

Male Crj:CD(ICR) mice of age 8 weeks were purchased from Charles River Japan, Inc. The mice were placed and fed in polycages in environment at room temperature of about 25° C. and a relative humidity of about 60% in a bright/dark cycle where the bright stage was set from 7:00 to 19:00. Up to age 87 weeks, the mice were fed with a commercially available solid feed CRF-1 (manufactured by Oriental Yeast Co., Ltd.), to promote the senility of the mice. Immediately before the age 88 weeks, the animals (mice) were assigned to two groups, namely a group with no-addition diet (n=25) and a group fed with an experimental diet [(methionine+threonine) diet] (n=27). The experimental diet was as follows. The experimental diet was fed for 2 weeks. During the period, 4 animals of the no-addition diet group died, while 3 animals of the (methionine+threonine) diet group died. Autopsy findings suggested that all the animals possibly ended in natural death. Finally, n=21 in the no-addition diet group and n=24 in the (methionine+threonine) diet group were made. As drinking water, tap water was fed ad libitum.

Experimental Feeds:

The no-addition diet and the experimental diet [(methionine+threonine) diet] were prepared in the same manner as in Example 1. Because the weight of mouse is considerably less than the weight of rat, smaller 2-% quantities of both methionine and threonine were blended, because of the difference in body weight.

Various Measurements:

Body weight and feed intake were measured. Table 2 shows body weight, total body weight increment, and total intake on week 2 from the start of the feeding of the experimental diet. Herein, the groups were compared together by the Student's t test in terms of individual measured items. At the level of significance, P<0.05, statistic significance was determined.

TABLE 2

| Experimental diet fed | Body weight at start of feeding[1,2] (g) | Body weight on week 2 from start of feeding[1,2] (g) | Body weight increment[1,2] (g/2 weeks) | Intake of experimental diet[1,2] (g/2 weeks) |
|---|---|---|---|---|
| No-addition diet | 49.8 ± 5.6 a | 49.2 ± 7.2 a | −0.6 ± 2.9 a | 65.6 ± 8.3 a |
| 2% methionine + 2% threonine diet | 49.4 ± 4.2 a | 43.7 ± 5.3 b | −5.7 ± 3.9 b | 48.5 ± 9.6 b |

[1] Numerical figure shows mean ± SD in the table.
[2] There is a statistical significance between different symbols "a" and "b" (at a 5% level of significance); and no significant difference between identical symbols.

Results:

2 weeks later after the start of feeding with the experimental diet, all of the body weight, body weight increment and experimental diet intake were significantly reduced in the (methionine+threonine) group. This indicates that the effect of the (methionine+threonine) blend diet on appetite loss as certified at the experiment about rats of aged 6 to 8 weeks in Example 1 is apparently exerted effectively in the different animal species (mice) and at senile stage (88 to 90 weeks old).

Example 5

Verification of Effect in Methionine Intake

Experimental Animals:

Male F344/DuCrj rats of age 6 weeks (5 animals; Charles River Japan, Inc.) preliminarily fed with a commercially available powder feed CRF-1 (Oriental Yeast Co., Ltd.) for one week were used. The same environmental conditions as described in Example 1 were used for the room temperature, humidity and bright and dark cycle of the feeding environment.

Experimental Feeds:

As described above in Example 1, a part of β-cornstarch in the experimental diet based on the AIN-93G composition (US NRC, 1995) was replaced with (by) methionine or threonine, so as to blend each of the amino acids in the experimental diet. The blend ratios of methionine and threonine in the resulting experimental diet were at 2.4% and 3.8%, respectively.

Experimental Method:

Two feeding boxes were arranged per one rat. One of the boxes contained the methionine diet, while the other contained the threonine diet. These two feeding boxes were simultaneously given to the individual rats, to measure body weight and feed intake daily. The measurement was continued for 2 weeks.

Results:

Table 3 below shows total body weight increment, total methionine diet intake, total threonine diet intake and total diets intake per individual (animal) over 2 weeks of feeding with the individual experimental diets.

TABLE 3

| | Experimental diet intake (g/2 weeks) | | | Body weight |
|---|---|---|---|---|
| Animal No. | 2.4% methionine diet | 3.8% threonine diet | total | increment (g/2 weeks) |
| 1 | 11.2 | 80.9 | 92.1 | 28.6 |
| 2 | 47.7 | 1.7 | 49.4 | −5.9 |

TABLE 3-continued

| | Experimental diet intake (g/2 weeks) | | | Body weight |
|---|---|---|---|---|
| Animal No. | 2.4% methionine diet | 3.8% threonine diet | total | increment (g/2 weeks) |
| 3 | 43.4 | 1.3 | 44.7 | −6.5 |
| 4 | 7.1 | 83.2 | 90.3 | 29.3 |
| 5 | 44.5 | 1.2 | 45.7 | −8.4 |

After the 2-week feeding with the individual experimental diets, 3 of the 5 animals selectively ingested the methionine diet, while the remaining 2 animals favored the threonine diet. Compared with the 2 animals favoring the threonine diet, additionally, the body weight increase of the 3 animals having selectively ingested the methionine diet had been suppressed apparently. This possibly indicates that the appetite loss or the suppression of body weight increase having been known as an action of a large dose of methionine is not an effect directly ascribed to the rejection of the intake of the methionine diet but a secondary action occurring in the biological organisms after methionine intake. Hence, the development of an appetite suppressor using methionine is highly possible in practical sense.

Example 6

Production of Methionine Dosage Form

For the production and dosing (the administration) of a methionine dosage form, it is the simplest way to mix together DL-methionine (1.0 g) and L-threonine (1.3 g) and seal the resulting mixture in a capsule. Besides, a method for producing a methionine tablet is suggested, including a step for adding powders or excipients to the resulting mixture. So as to obtain or recover the effect of appetite loss from these dosage forms (preparations), these dosage forms may be given, for example three times daily, 30 to 60 minutes before meals.

Example 7

Production of Diet Food

Table 4 below shows a composition as one example of a dietary food (diet food) complying with the Recommended Diet Allowances Standard in the dosage three times daily and having a possible effect on appetite loss (appetite lowering) toward foods other than the dietary food.

TABLE 4

| Composition for use in dietary food (energy: 800 kcal per one meal) | |
|---|---|
| DL-Methionine | 1.0 g |
| L-Threonine | 1.3 g |
| Protein | 23.6 g |
| Lipid | 17.8 g |
| Carbohydrate | 134.1 g |
| Sodium | 867 mg |
| Potassium | 667 mg |
| Calcium | 200 mg |
| Iron | 3.3 mg |
| Magnesium | 83 mg |
| Phosphorus | 233 mg |
| Vitamin A | 600 IU |
| Vitamin B1 | 0.3 mg |
| Vitamin B2 | 0.3 mg |
| Vitamin B6 | 0.4 mg |
| Vitamin B12 | 0.8 μg |
| Niacin | 4.3 mg |
| Pantothenic acid | 1.7 mg |
| Folic acid | 67 μg |
| Vitamin C | 33 mg |
| Vitamin D | 33 mg |
| Vitamin E | 2.7 mg |
| Dietary fiber | 6.7 g |

Foods in the forms of drinks and sweets and other forms are exemplified, which can be readily ingested orally and can be packed in portable wrapping materials. Further, the addition of flavoring agents, sweeteners, spices and the like is also exemplified so as to permit easy oral ingestion.

Effect of the Invention

In accordance with the present invention, a suppressor of anemia containing (comprising) threonine as an effective ingredient, preferably a suppressor of hemolytic anemia due to methionine is provided. In addition, an appetite suppressor containing (comprising) a combination of methionine and threonine as effective ingredients can be provided as well.

Because, in particular the significant side effects of methionine namely reticulocyte increase and iron deposition on spleen can be ameliorated (reduced) selectively, the use of methionine having been restricted in the fields of nutritious supplements, pharmaceutical products and foods and drinks due to the side effects will possibly be enlarged from the respects of volume and applicability with expectation. Particularly, the inventive product is highly promising as a safe appetite suppressor with reduced hemolytic anemia.

This application is based on Japanese Patent Application No. 2001-165242, filed on May 31, 2001, and on Internal Japanese Patent Application No. 2002-150918, filed on May 24, 2002, both of which are incorporated herein by reference in their entireties.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method for suppressing appetite, comprising:
administering to a subject in need thereof an appetite-suppressing effective amount of methionine or a salt thereof and administering to the subject an effective amount of an anemia-suppressing composition, wherein: said anemia-suppressing composition comprises an anemia-suppressing effective amount of threonine or a salt thereof;
said methionine is administered in an amount of 25 to 100 mg/kg/day on the basis of the free form of methionine; said threonine is administered in an amount of 20 to 300 mg/kg/day on the basis of the free form of threonine; said anemia-suppressing composition comprises less than 5% by weight of glycine; and said anemia-suppressing composition comprises less than 1% by weight of serine.

2. The method of claim 1, wherein said methionine and said threonine are administered in a ratio of threonine to methionine of 80 to 300% (by weight) on the basis of the free forms of methionine and threonine.

3. The method of claim 1, wherein said anemia-suppressing composition comprises less than 1% by weight of glycine.

4. The method of claim 1, wherein said anemia-suppressing composition comprises less than 0.1% by weight of glycine.

5. The method of claim 1, wherein said anemia-suppressing composition comprises less than 0.1% by weight of serine.

* * * * *